United States Patent
Carpenter

(10) Patent No.: US 10,238,417 B1
(45) Date of Patent: Mar. 26, 2019

(54) CURETTE WITH LIGHT

(71) Applicant: Shaun R. Carpenter, Mandeville, LA (US)

(72) Inventor: Shaun R. Carpenter, Mandeville, LA (US)

( * ) Notice: Subject to any disclaimer, the term of this patent is extended or adjusted under 35 U.S.C. 154(b) by 802 days.

(21) Appl. No.: 14/491,842

(22) Filed: Sep. 19, 2014

Related U.S. Application Data

(60) Provisional application No. 61/983,319, filed on Apr. 23, 2014, provisional application No. 61/879,944, filed on Sep. 19, 2013.

(51) Int. Cl.
| | | |
|---|---|---|
| *A61B 17/3207* | (2006.01) | |
| *A61B 19/00* | (2006.01) | |
| *A61D 1/00* | (2006.01) | |
| *A61B 17/00* | (2006.01) | |

(52) U.S. Cl.
CPC ...... *A61B 17/320708* (2013.01); *A61B 19/46* (2013.01); *A61B 19/5202* (2013.01); *A61D 1/00* (2013.01); *A61B 2017/0023* (2013.01); *A61B 2017/320733* (2013.01); *A61B 2019/461* (2013.01); *A61B 2019/521* (2013.01)

(58) Field of Classification Search
CPC ....... A61B 2017/320733; A61B 2017/320004; A61B 2017/320008
See application file for complete search history.

(56) References Cited

U.S. PATENT DOCUMENTS

| | | | | |
|---|---|---|---|---|
| 651,395 A | * | 6/1900 | Stapp | A61B 17/320708 606/160 |
| 3,502,082 A | | 3/1970 | Chatfield | |
| 3,635,222 A | * | 1/1972 | Robinson | A61B 17/320708 128/840 |
| 3,929,138 A | * | 12/1975 | Curi | A61B 17/320708 606/167 |
| 4,044,770 A | * | 8/1977 | Ocel | A61B 17/320708 606/161 |
| 5,116,346 A | | 5/1992 | Yeh | |
| 5,282,816 A | * | 2/1994 | Miller | A61B 17/1659 606/167 |
| 5,902,314 A | * | 5/1999 | Koch | A61B 17/50 606/160 |
| 5,925,056 A | | 7/1999 | Thomas et al. | |
| 5,968,062 A | | 10/1999 | Thomas et al. | |

(Continued)

OTHER PUBLICATIONS

Scanlan International, Inc., Vented Tip-Guard Instrument Protectors and Integra Miltex, BiopBlade.

*Primary Examiner* — Alexander Orkin
(74) *Attorney, Agent, or Firm* — Garvey, Smith & Nehrbass, Patent Attorneys, L.L.C.; Charles C. Garvey, Jr.; Mackenzie D. Rodriguez

(57) ABSTRACT

Improvements for curettes currently used in debridement and removal of skin, tissue, and necrotic debris from wound beds comprising a pinchable cap and a circular metal cutting end, wherein an individual may preferably apply pressure to the cap, preferably covering the metal cutting end, in order to manipulate the cutting end into a shape to preferably debride narrow or smaller portions of a wounds such as a narrow oval. The surgical instrument also preferably includes a measurement scale, a depth probe that also acts as a packing tool, and finger grips. There can be an optional LED or LEDs included in or on the curette.

17 Claims, 10 Drawing Sheets

(56) References Cited

U.S. PATENT DOCUMENTS

| | | | |
|---|---|---|---|
| 6,001,113 A | 12/1999 | Goldblum | |
| 6,679,897 B2 | 1/2004 | Josephson | |
| 7,587,992 B2 | 9/2009 | Dunn et al. | |
| 2006/0111722 A1* | 5/2006 | Bouadi | A61B 17/1604 606/79 |
| 2007/0288042 A1 | 12/2007 | Serbousek et al. | |
| 2008/0103504 A1* | 5/2008 | Schmitz | A61B 17/320016 606/79 |
| 2012/0265228 A1 | 10/2012 | Peterson | |
| 2013/0190647 A1* | 7/2013 | Pahuja | A61B 5/1076 600/559 |

* cited by examiner

Squeeze cap to re-shape scraping end

CURETTE WITH LIGHT

CROSS-REFERENCE TO RELATED APPLICATIONS

Priority of U.S. Provisional Patent Application Ser. No. 61/879,944, filed 19 Sep. 2013, and U.S. Provisional Patent Application Ser. No. 61/983,319, filed 23 Apr. 2014, both of which are incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to methods of and apparatus for debridement and removal of skin, tissue, and necrotic debris from wound beds. More particularly, the present invention relates to a surgical instrument such as a curette comprising a pinchable clear cap and a circular metal cutting end, wherein an individual may preferably apply pressure to the cap, preferably covering the metal cutting end, allowing for said pressure to be transferred from the cap to the cutting end when the cap comes in contact with the cutting end in order to preferably manipulate the cutting end into a shape to preferably debride narrow or smaller portions of a wounds such as a narrow oval. The cap is preferably clear or translucent. The surgical instrument also preferably includes a measurement scale, a depth probe that also acts as a packing tool, and finger grips. There can be an optional LED or LEDs included in or on the curette.

2. General Background of the Invention

Current curettes with flexible band loop blades for wound debridement do not include means for effectively manipulating the band to debride narrow or smaller portions of a wound. Furthermore, these curettes do not include features for protecting an individual from injury when using the curettes.

The following references are incorporated herein by reference: U.S. Pat. Nos.: 3,502,082; 5,116,346; 5,925,056; 5,968,062; 6,001,113; 6,679,897; 7,587,992; U.S. Patent Application Publication Document Nos.: 2007/0288042; and 2012/0265228.

The following publications are hereby incorporated herein by reference:

Scanlan International, Inc., *Vented Tip-Guard Instrument Protectors* and Integra Miltex, *BiopBlade*.

BRIEF SUMMARY OF THE INVENTION

The present invention solves the shortcomings in the field by providing an improved apparatus by advancing the utility of a traditional curette.

The present invention relates to a method of and apparatus for debridement and removal of skin, tissue, and necrotic debris from wound beds. More particularly, the present invention relates to a surgical instrument such as a curette comprising a pinchable cap and a circular metal cutting end, wherein an individual may preferably apply pressure to the cap, preferably covering the metal cutting end, allowing for said pressure to be transferred from the cap to the cutting end when the cap comes in contact with the cutting end in order to preferably manipulate the cutting end into a shape to preferably debride narrow or smaller portions of a wounds such as a narrow oval. The cap is preferably clear or translucent. The surgical instrument also preferably includes a measurement scale, a depth probe that also acts as a packing tool, and finger grips. There can be an optional light emitting diode (LED) or LEDs included in or on the curette.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

A preferred embodiment of the present invention, an apparatus 10 for a surgical instrument such as a curette 11, is shown in FIGS. 1-7. The surgical instrument 11 is preferably intended for single patient/animal encounter use in the debridement and removal of skin, tissue, and necrotic debris from wound beds. The apparatus 10 is preferably disposable and is preferably intended for single patient/animal encounter use in the debridement and removal of skin, tissue, and necrotic debris from wound beds.

Figure 1:
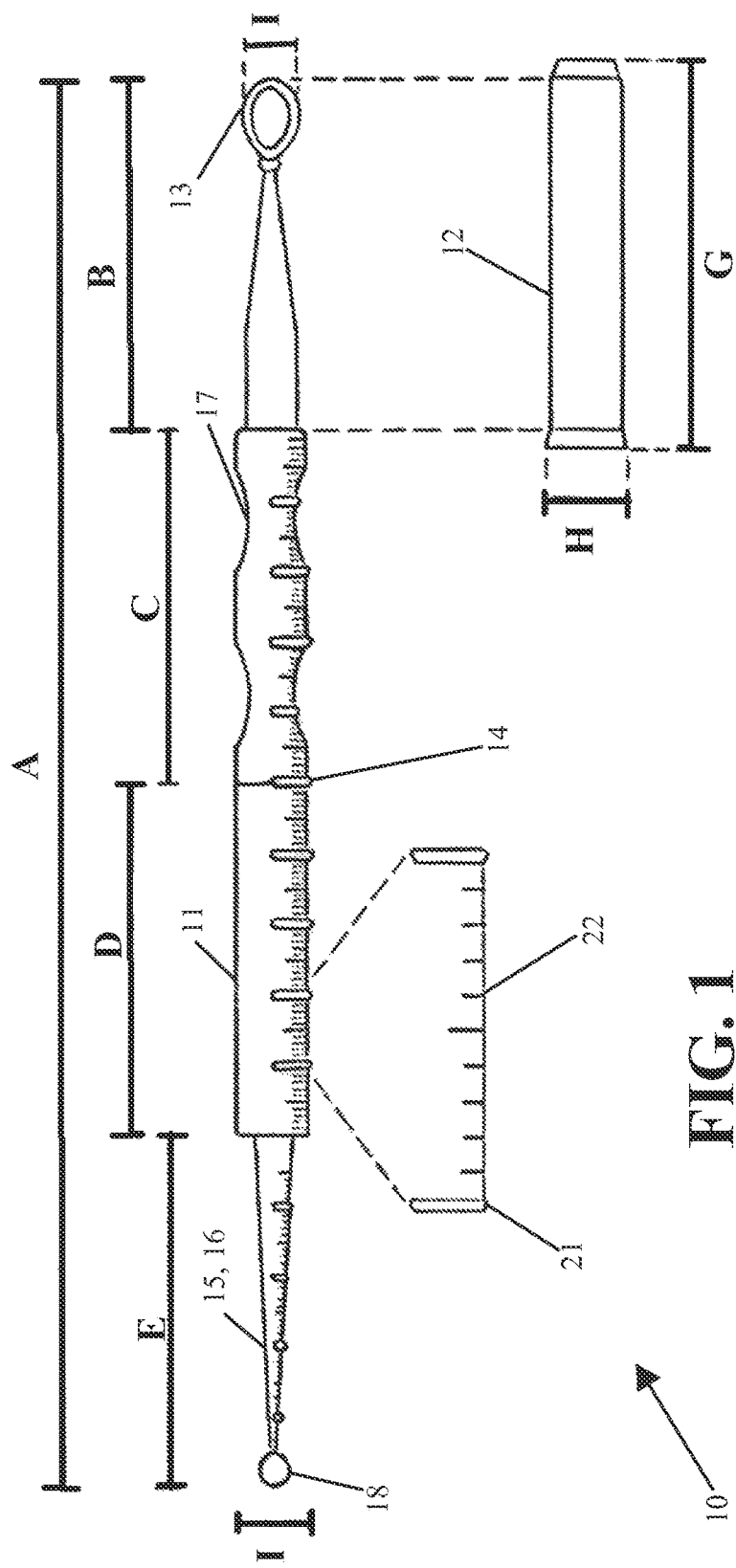
FIG. 1 shows a side view of a preferred embodiment of the present invention where the metal cutting end has been pinched.
Figure 2:
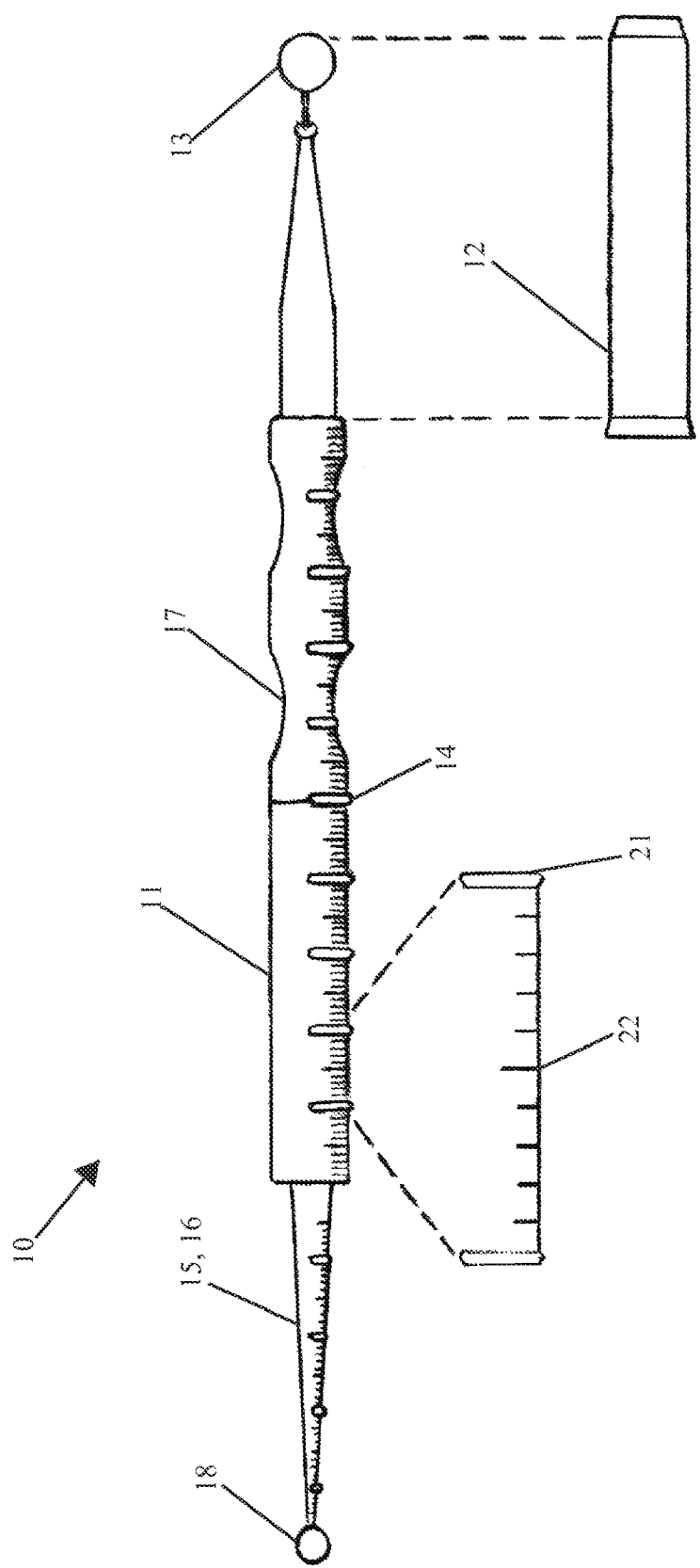
FIG. 2 shows a side view of a preferred embodiment of the present invention.
Figure 3:
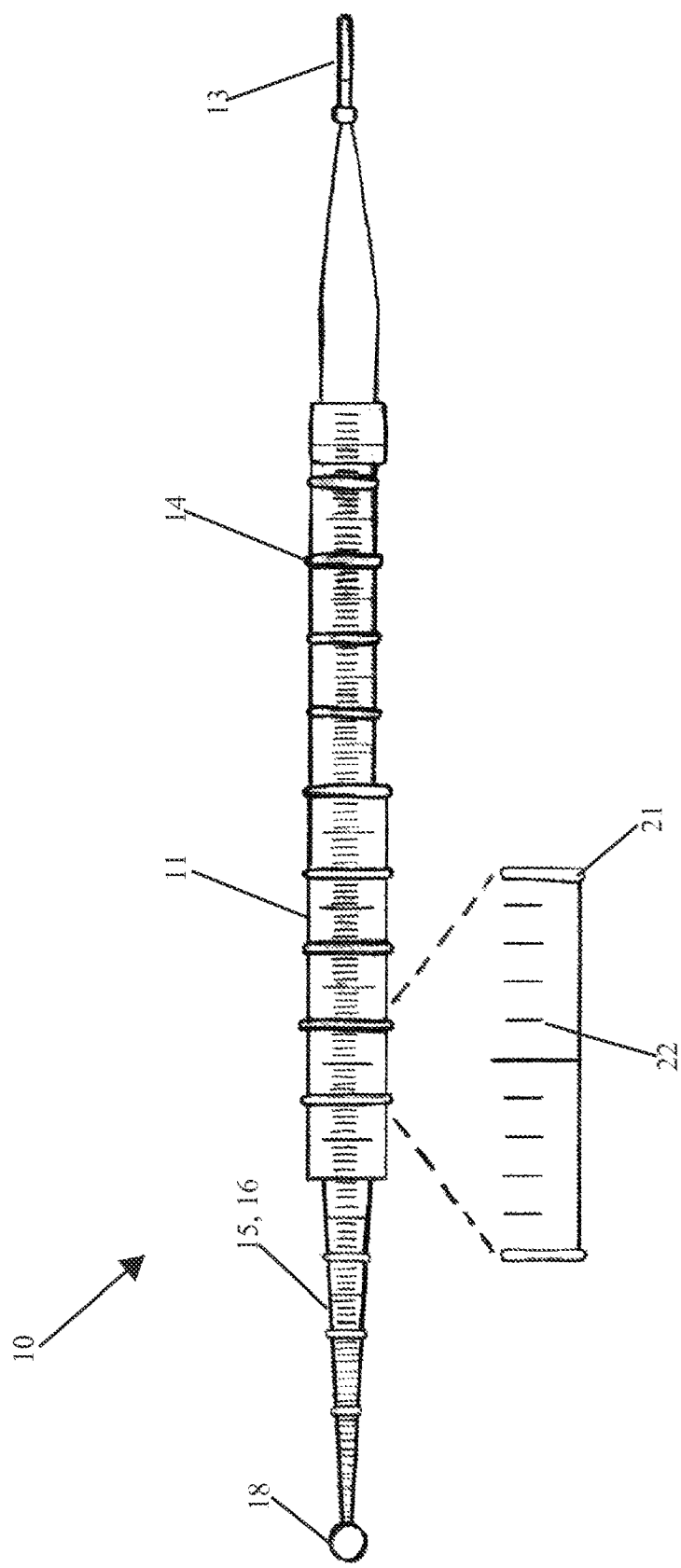
FIG. 3 shows a rotated side view of a preferred embodiment of the present invention.

FIGS. 1-3 show side views of the apparatus 10. The apparatus 10 is a surgical instrument such as a curette 11 including a clear pinchable cap 12 and a circular metal cutting end 13, wherein an individual may preferably pinch the cap 12 preferably covering the metal cutting end 13 in order to preferably manipulate the cutting end 13 into a shape to preferably debride narrow or smaller portions of a wounds such as a narrow oval. The surgical instrument also preferably includes a measurement scale 14, a depth probe 15 that also acts as a packing tool 16, and finger grips 17.

FIG. 1 shows a side view of any embodiment of the present invention with a length "A". Length "A" preferably ranges from 25 cm to 5 cm. More preferably, length "A" ranges from 20 cm to 10 cm. Most preferably, length "A" ranges from 20 cm to 15 cm. In another embodiment of the present invention, length "A" is 19.5 cm.

The curette 11 of any embodiment of the present invention is preferably made up of plastic. Alternatively, the curette of any embodiment of the present invention can be made of plastic, steel, or titanium.

FIG. 1 show a side view of a section of the curette 11 including the cutting end 13 of any embodiment of the present invention with a length "B" and the cutting end of any embodiment of the present invention with a diameter "F".

Figure 4:
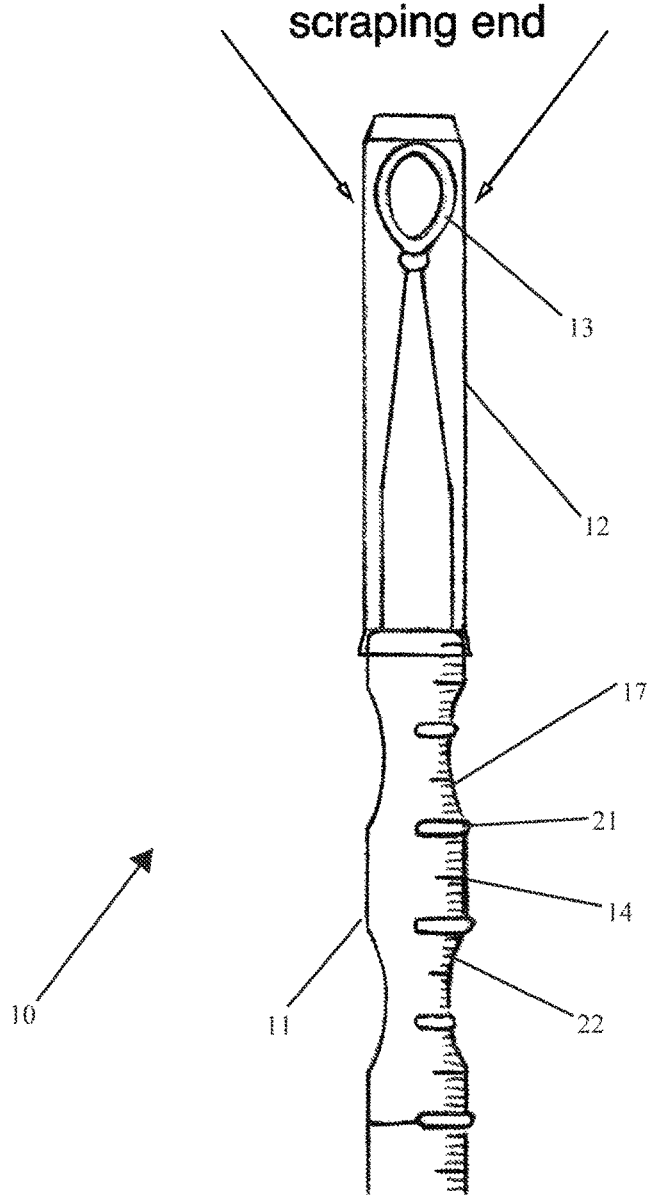
FIG. 4 shows an enlarged view of a preferred embodiment of the present invention where the cap has been placed over the curette and the metal cutting end.
Figure 5:
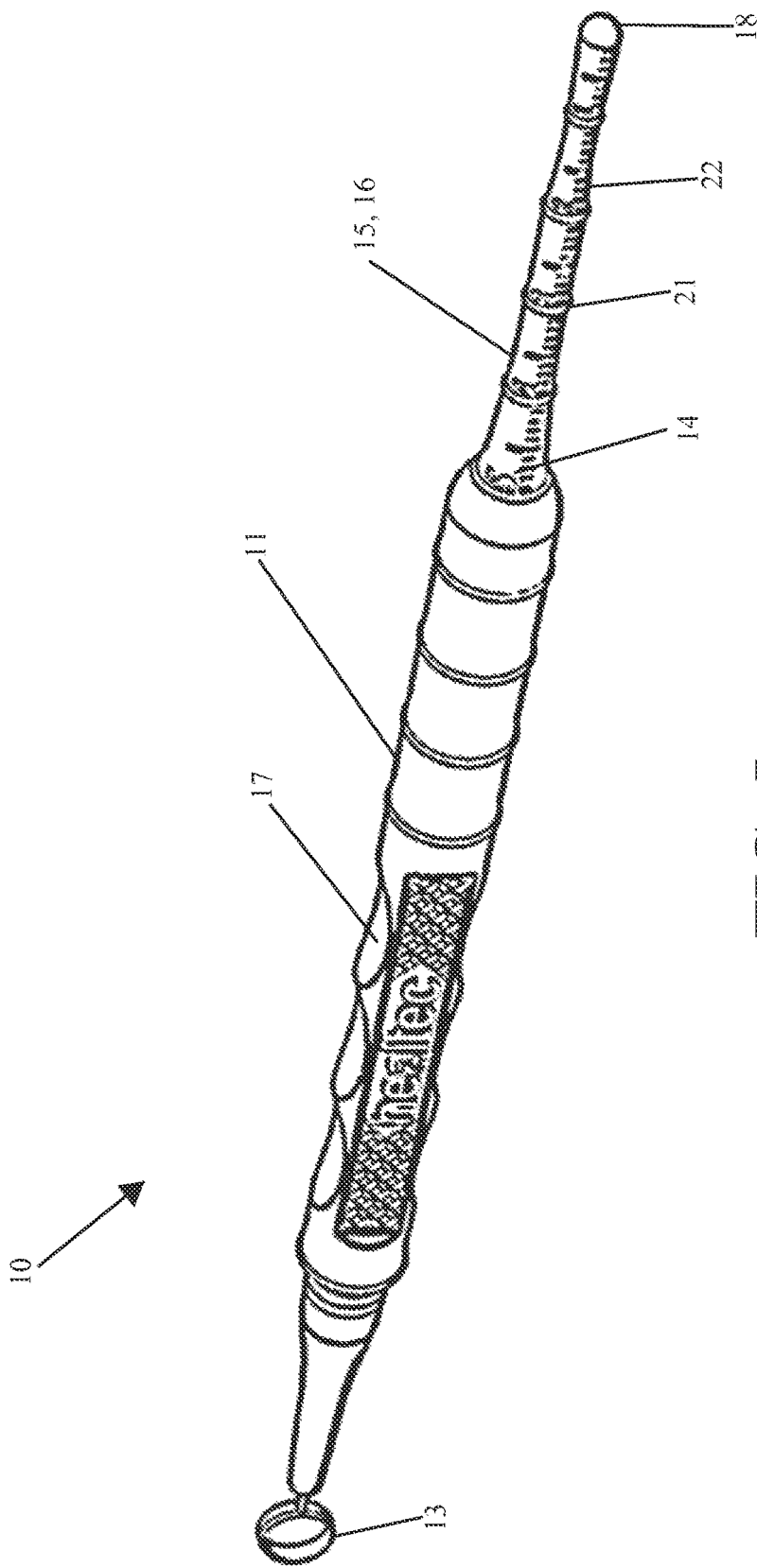
FIG. 5 shows a perspective view of a preferred embodiment of the present invention with three finger grooves and a double-edged circular metal cutting head.
Figure 6:
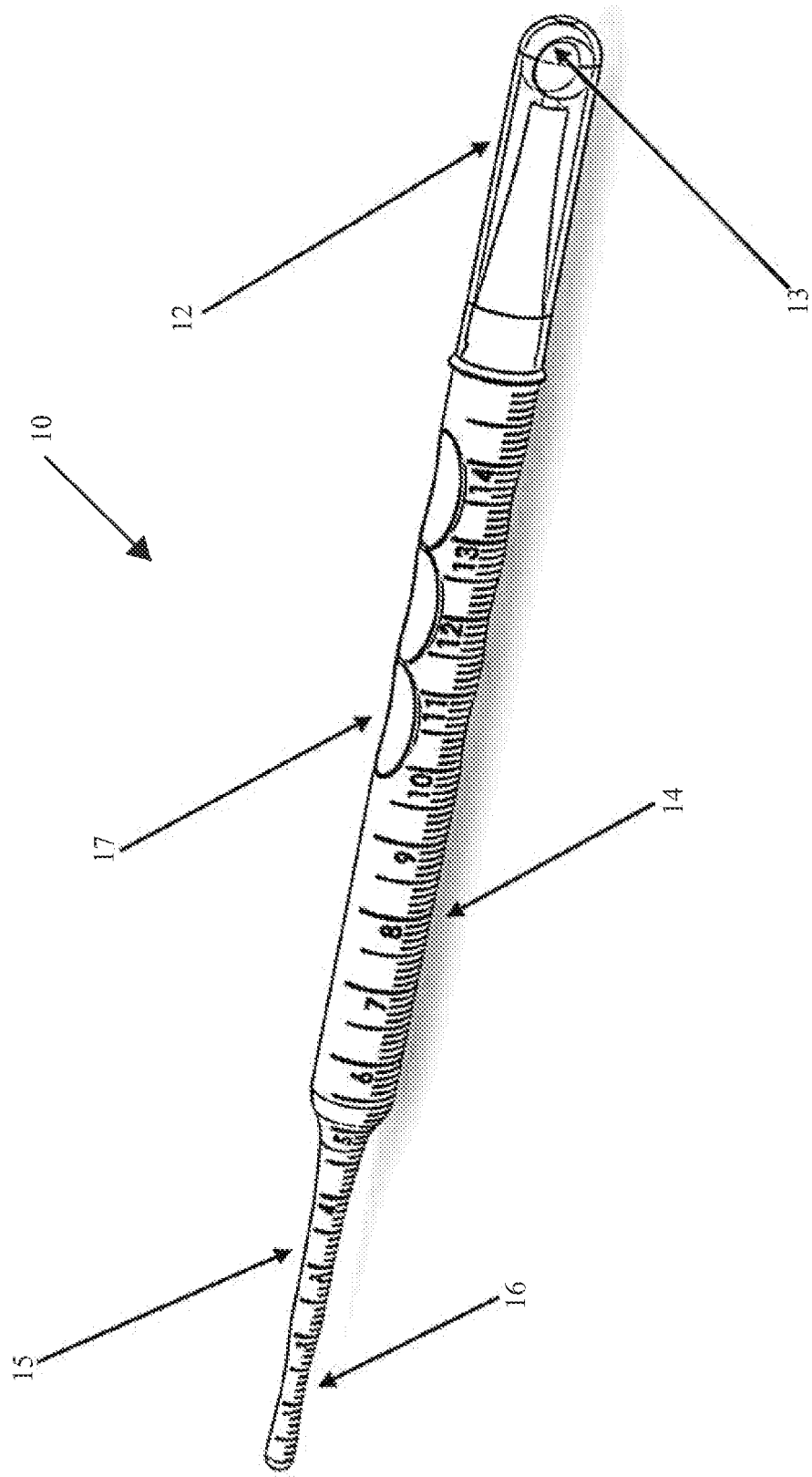
FIG. 6 shows a perspective view of a preferred embodiment of the present invention with three finger grooves and a double-edged circular metal cutting head.
Figure 7:
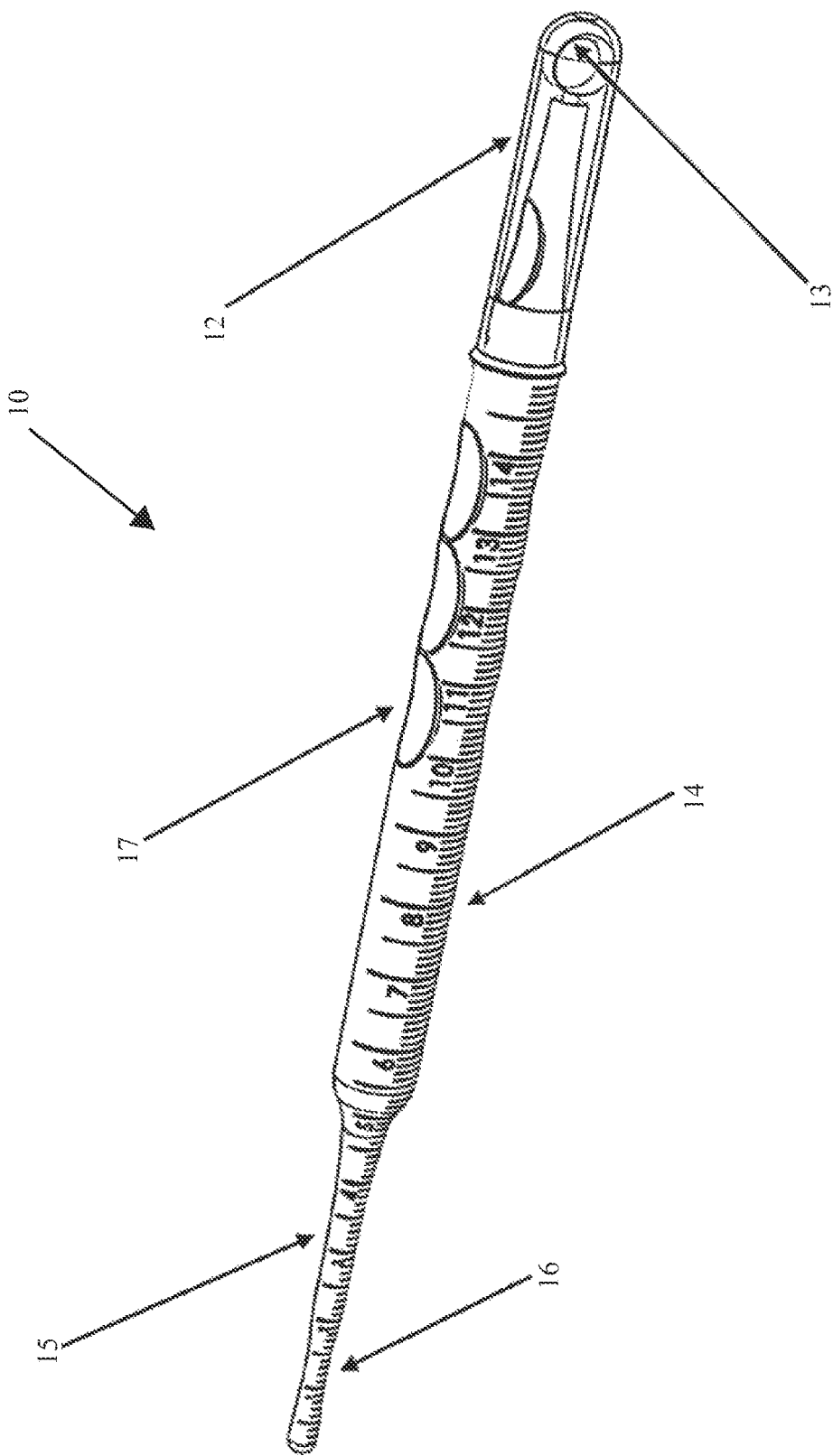
FIG. 7 shows a perspective view of a preferred embodiment of the present invention with four finger grooves and a double-edged circular metal cutting head.
Figure 8:
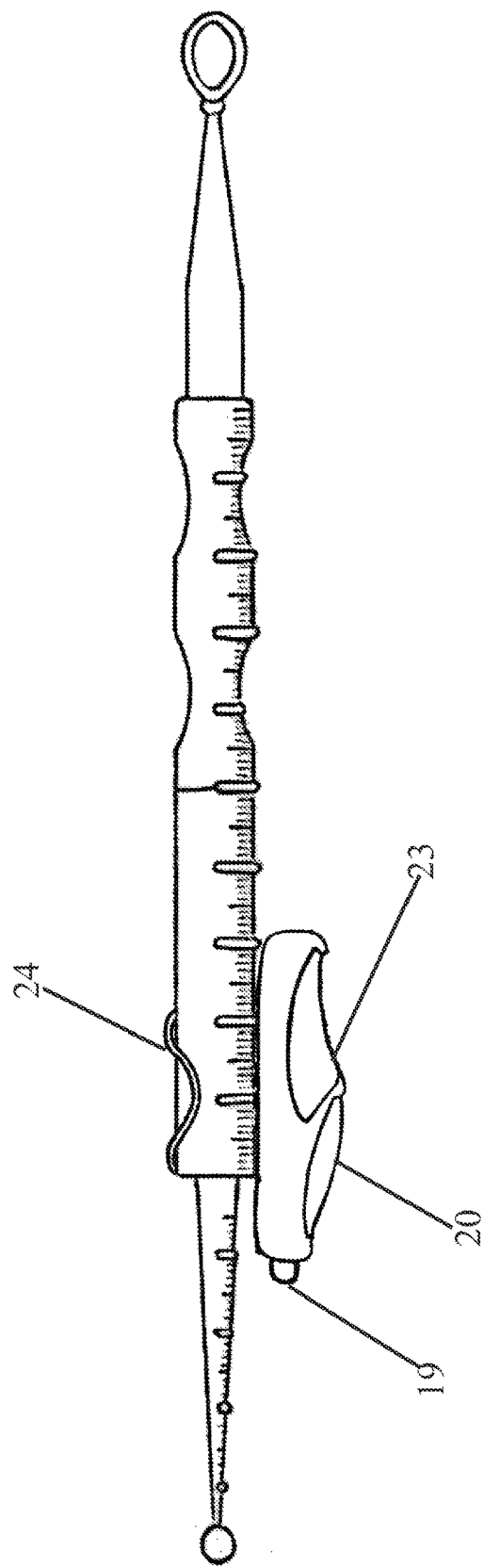
FIG. 8 shows a side view of an embodiment of the present invention including a clip-on LED attached to the curette and positioned adjacent to the depth probe.
Figure 9:
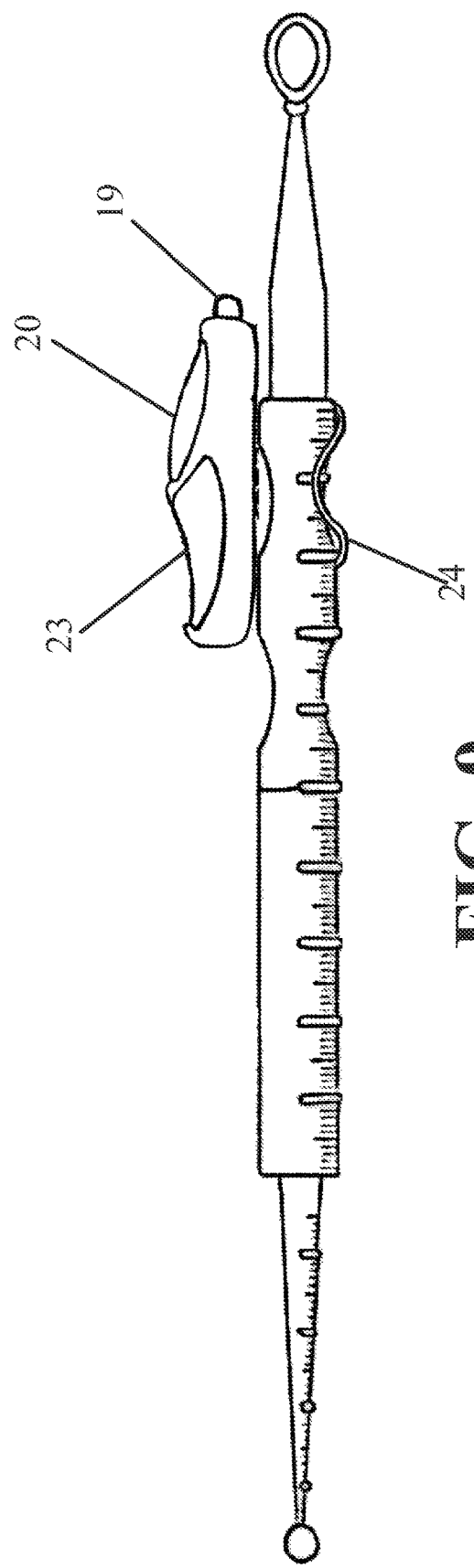
FIG. 9 shows a side view of an embodiment of the present invention including a clip-on LED attached to the curette and positioned adjacent to the section of the curette including the metal cutting head.
Figure 10:
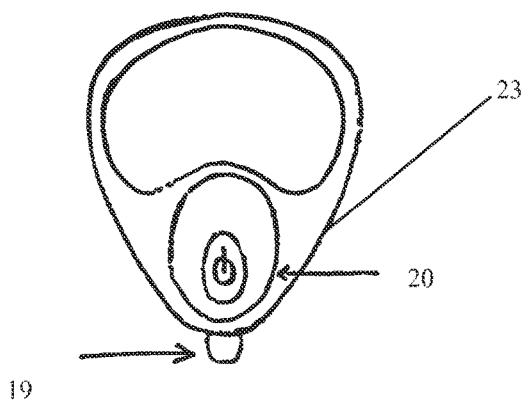
FIG. 10 shows a top view of the clip-on LED.
Figure 11:
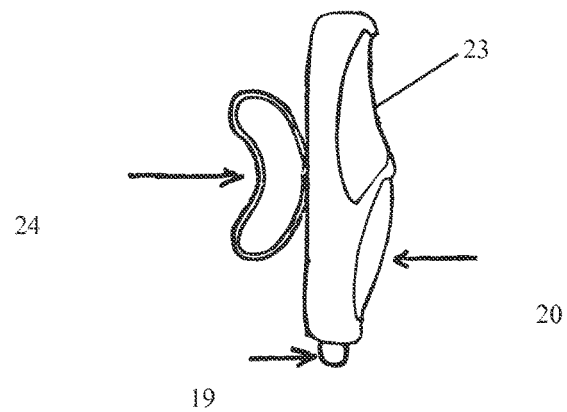
FIG. 11 shows a side view of the clip-on LED.

As shown in FIGS. 1-7, the circular metal cutting head 13 is preferably sharp and flexible enough to be molded using the pinchable cap 12 as shown in FIGS. 1 and 4. The circular metal cutting head 13 is preferably made of a type of metals (such as hardened and tempered steel, stainless steel, or high carbon steel) that is preferably able to hold an edge and preferably maintain sharpness longer than traditional curettes, even after cutting through bone, tendon, and muscle. An alternative embodiment of the invention as shown in FIGS. 5-7 includes circular metal cutting head 13 being double-edged, so that the cutting head 13 can preferably cut using either the top or bottom edge of the head.

As shown in FIG. 1, length "B" preferably ranges from 5 cm to 2 cm. More preferably, length "B" ranges from 4.5 cm to 3 cm. Most preferably, length "B" ranges from 4 cm to 3 cm. In a preferred embodiment of the present invention, length "B" is 3.5 cm.

As shown in FIG. 1, diameter "F" preferably ranges from 10 mm to 0.5 mm. More preferably, diameter "F" ranges from 8 mm to 4 mm. Most preferably, diameter "F" ranges from 9 mm to 7 mm. In a preferred embodiment of the present invention, diameter "F" is 7 mm.

FIG. 1 show a side view of the cap of any embodiment of the present invention with a length "G" and a diameter "H".

As shown in FIGS. 1, 4, and 5, the clear, pinchable cap 12 preferably allows an individual to pinch the circular metal cutting end 13 and preferably mold the cutting end into a more applicable shape such as a narrow oval whenever needed to debride narrow or smaller portions of a wounds. The cap 13 is preferably clear or translucent. The cap 13 is preferably made up of soft plastic. Alternatively, the cap can be made of rubber, plastic, or silicone. The clear cap 13 preferably allows an individual to see the metal circular cutting head 12, and safely pinch it to the desired diameter and shape, without cutting one's fingers. Although the cutting head 13 preferably starts out as a circle with for example a 7 mm diameter, the cutting head 13 can be preferably pinched down to a very narrow (such as 1 mm diameter) ovoid shape.

As shown in FIG. 1, length "G" preferably ranges from 5 cm to 2 cm. More preferably, length "G" ranges from 4.5 cm to 3.0 cm. Most preferably, length "G" ranges from 4 cm to 3 cm. In a preferred embodiment of the present invention, length "G" is 3.5 cm.

As shown in FIG. 1, diameter "H" preferably ranges from 20 mm to 5 mm. More preferably, diameter "H" ranges from 15 mm to 8 mm. Most preferably, diameter "H" ranges from 12 mm to 10 mm. In a preferred embodiment of the present invention, diameter "H" is 12 mm.

FIG. 1 shows a side view of sections of the curette 11 including a measurement scale 14 of any embodiment of the present invention with length "C", "D", and "E". As shown in FIGS. 1-7, the measurement scale 14 preferably includes markings for centimeter 21 and millimeter measurements 22. The measurement scale 14 preferably includes a range from 0 to 15 centimeters, with millimeter hash marks preferably included for finer measurement. The measurement scale 14 turns the curette into a measurement device.

FIG. 1 shows a side view of sections of the curette 11 including a measurement scale of any embodiment of the present invention with a length "D". The measurement scale 11 of sections of the curette with a length "D" preferably includes a scale with markings 21, 22 indicating centimeter and millimeter. In alternative embodiment, the measurement scale includes United States customary units of length or known units of measure.

As shown in FIG. 1, length "D" preferably ranges from 10 cm to 2 cm. More preferably, length "D" ranges from 8 cm to 4 cm. Most preferably, length "D" ranges from 7 cm to 5 cm. In a preferred embodiment of the present invention, length "D" is 5 cm.

FIG. 1 shows a side view of a depth probe 15 with a ball tip 18 of any embodiment of the present invention with a length "E" and the ball tip 18 with a diameter "I". As shown in FIGS. 1-7, the depth probe 15 preferably tapers to an end of the curette which preferably allows for measuring the depth of wounds, such as small-diameter tunneling wounds. Preferably attached to the depth probe 15 at the end of the curette is a ball tip 18 depth probe 15 that is preferably in a teardrop or ball shape to give the tip 18 of the depth probe 15 a smooth, rounded shape. The smooth, rounded shape of the tip 18 will preferably decrease the chance of puncturing hidden vital structures such as arteries, bowel, etc.

The depth probe 15 also preferably serves as a packing tool 16, allowing an individual to preferably pack wound dressings into wound cavities easily. Although tapered and narrow, the packing tool 16 is preferably strong enough so that it won't break off under high force loads. The packing tool 16 is also preferably made out of flexible polymers (such as ethylene copolymers, resins, PET Polyesters, or elastomers) so that it can preferably measure curved wound tunnel depth. Alternatively, the tool 16 can be made of steel, aluminum, or plastic.

As shown in FIGS. 1-7, the depth probe 15 also preferably includes a measurement scale 14. The measurement scale 14 of the depth probe 15 with a length "E" preferably includes a scale with markings 21, 22 indicating centimeter and millimeter. In alternative embodiment, the measurement scale includes United States customary units of length or known units of measure.

As shown in FIG. 1, length "E" preferably ranges from 10 cm to 1 cm. Most preferably, length "E" ranges from 8 cm to 4 cm. In a preferred embodiment of the present invention, length "E" is 5 cm.

As shown in FIG. 1, diameter "I" preferably ranges from 12 mm to 2 mm. Most preferably, diameter "I" ranges from 10 mm to 5 mm. In a preferred embodiment of the present invention, diameter "H" is 7 mm.

FIG. 1 shows a section of the curette of an embodiment of the present invention with finger grips 17 comprising two finger grooves and a length "C". FIGS. 5 and 6 shows a section of the curette of an embodiment of the present invention with finger grips 17 comprising three finger grooves. FIG. 7 shows a section of the curette of an embodiment of the present invention with finger grips 17 comprising four finger grooves, wherein the finger groove closest to the metal cutting end is preferably covered by the cap when the cutting end is being manipulated.

As shown in FIGS. 1-7, the finger grips 17 of the curette 11 preferably have 2-4 finger grooves which give an individual better grip of the instrument, and more positions with which to hold the instrument depending on hand size.

The section of the curette 11 with finger grips 17 also preferably includes a measurement scale 14. The measurement scale 14 of the section with finger grips preferably include a scale with markings 21, 22 indicating centimeter and millimeter. In alternative embodiment, the measurement scale 14 includes United States customary units of length or known units of measure.

As shown in FIG. 1, length "C" preferably ranges from 10 cm to 1 cm. More preferably, length "C" ranges from 8 cm to 3 cm. Most preferably, length "C" ranges from 6 cm to 4 cm. In another embodiment of the present invention, length "C" is 5 cm.

The top of the curette 11 is preferably marked with the word "TOP" to preferably alert an individual as to which way to hold the curette to keep the cutting head toward the wound bed.

In a preferred embodiment, the invention includes one or more LED lights 19. The LED light 19 can be in one of a variety of locations, or in multiple locations, such as on either end, or both ends. Preferably, there is a push button 20 (or other suitable switch) on the apparatus of the invention to turn the LED light 19 or lights off and on.

Shown in FIGS. 8-11 is clip-on LED 23, an example of how an LED light can be included with the curette of the present invention. The LED 19 is preferably pointed toward cutting end 13 as shown in the drawings. The clip-on LED of a commercial embodiment of the present invention will likely be more snug and sleek than that shown in these Figures, and more flush to the curette, and likely smaller, and even more likely much smaller. It can be, for example, about 5 mm wide by about 5 mm in thickness by about 1 cm long to about 1 cm wide by 1 cm in thickness to about 2 cm long.

The clip 24 could for example be made of flexible plastic or metal or rubber. It is preferably sized to provide a snug fit when clipped on to the curette 11. The LED clip-on light module can be powered by a battery or other suitable small power source.

The following is a list of parts and materials suitable for use in the present invention.

| PARTS LIST | |
|---|---|
| PART NUMBER | DESCRIPTION |
| 10 | apparatus |
| 11 | curette |
| 12 | cap |
| 13 | circular metal cutting end |
| 14 | measurement scale |
| 15 | depth probe |
| 16 | packing tool |
| 17 | finger grips/grooves |
| 18 | tip |
| 19 | LED lights |
| 20 | push button |
| 21 | centimeter markings |
| 22 | millimeter markings |
| 23 | clip-on LED module |
| 24 | curette clip |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. Apparatus including a curette used for debridement or removal of skin, tissue, and necrotic debris from wound beds comprising
   a) an instrument body having proximal and distal end portions;
   b) a circular metal cutting end on said distal end portion of said instrument body;
   c) a handle on said instrument body;
   d) a cap having an open end, a closed end and a hollow cavity, wherein said cap is of a soft moveable material that enables a user to pinch the cap and reconfigure the shape of the metal cutting end to an oval shape; and
   e) wherein the circular metal cutting end is attached to said distal end of the tool body and can be covered by the cap,
   f) wherein said cap is configured to move between a first position wherein the cap is placed over the metal cutting end and a second position wherein the cap is removed from and spaced away from the instrument body;
   g) wherein the apparatus has a length of 5-25 cm, and the circular metal cutting end has a diameter of 2-12 mm, and;
   h) wherein when the cap is in said first position, pressure can be applied to the cap by a user, the cap enables contact of the metal cutting end and wherein the pressure applied by a user is transferred from the cap to the cutting end allowing the cutting end to be manipulated into shapes suitable for debriding narrow or smaller portions of the wound bed.

2. The apparatus of claim 1, wherein the cap can be detached from the curette.

3. The apparatus of claim 1, wherein the shape of the circular metal cutting end starts as a circle and can be pinched down to an oval.

4. The apparatus of claim 1, wherein the circular metal cutting end is made of steel.

5. The apparatus of claim 1, wherein the circular metal cutting end is double-edged.

6. The apparatus of claim 1, wherein the apparatus is disposable and is for a single patient/animal encounter use.

7. The apparatus of claim 1, further comprising an LED on the curette.

8. The apparatus of claim 1, wherein the instrument body has a distal end and a proximal end and the metal cutting edge is located at the distal end, the apparatus further comprising one or more of the following:
   a) a measurement scale located along the length of the handle;
   b) a depth probe located at the distal end of the handle;
   c) a ball tip depth probe located at the proximal end of the handle;
   d) finger grips on the handle; and
   e) at least one LED light.

9. The apparatus of claim 8, wherein the depth probe is also a packing tool.

10. The apparatus of claim 9, wherein the packing tool is strong enough to handle high force loads.

11. The apparatus of claim 9, wherein the packing tool is made of flexible polymers.

12. The apparatus of claim 8, wherein the measurement scale includes hash marks on the apparatus that allows the apparatus to be a measurement device.

13. The apparatus of claim 8, wherein a ball tip depth probe is attached to the depth probe at an end of the apparatus, the ball tip depth probe having a teardrop or ball shape.

14. The apparatus of claim 8, wherein the apparatus is marked to alert an individual as to which way to hold the apparatus to keep the cutting end toward the wound bed.

15. The apparatus of claim 8, wherein the depth probe is also a packing tool.

16. The apparatus of claim 8, wherein the ball tip depth probe is a teardrop or ball shape.

17. A method of using the apparatus of claim 8, wherein an individual uses the apparatus for debridement or removal of skin, tissue, and necrotic debris from wound beds.

* * * * *